United States Patent [19]

Yatsu et al.

[11] Patent Number: 5,677,277
[45] Date of Patent: Oct. 14, 1997

[54] BRAIN ENDOTHELIAL CELL PROTEIN INDUCED BY NERVE GROWTH FACTOR

[75] Inventors: Frank M. Yatsu, Houston; Nargis A. Alam; Syed S. Alam, both of Webster, all of Tex.

[73] Assignee: Research Development Foundation, Carson City, Nev.

[21] Appl. No.: 239,889

[22] Filed: May 9, 1994

[51] Int. Cl.$^6$ .......................... A61K 38/00; A61K 38/03; C07K 14/47

[52] U.S. Cl. .................... 514/12; 530/350; 514/2

[58] Field of Search ................. 514/12; 530/350

[56] References Cited

PUBLICATIONS

Lillieu et al Nature 317 632-634 (1985).

Cordon-Cardo et al Cell 66 173-184 (1991).

Ikedo et al Brain Res 649 260-264 (1994).

*Primary Examiner*—Garnette D. Draper
*Assistant Examiner*—Elizabeth C. Kemmerer
*Attorney, Agent, or Firm*—Benjamin Aaron Adler

[57] ABSTRACT

The present invention provides a novel isolated and purified protein that is produced by brain endothelial cells, has a molecular weight of approximately 67 kDa of SDS-PAGE, with the protein being capable of stimulating proliferation of cerebral arteriole smooth muscle cells. Also provided are various methods of using this novel protein or the gene encoding this protein, including methods of treating various cerebrovascular diseases.

2 Claims, 7 Drawing Sheets

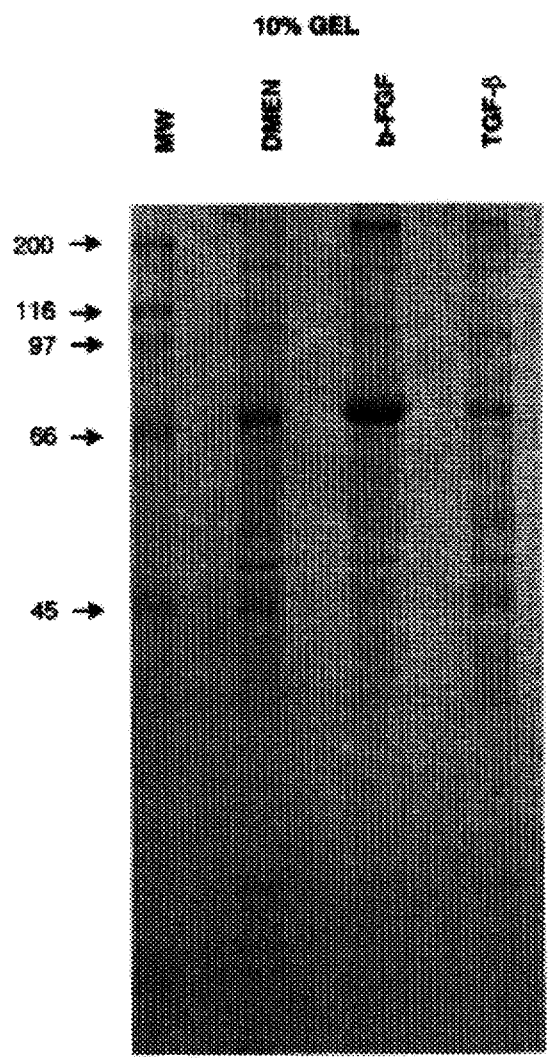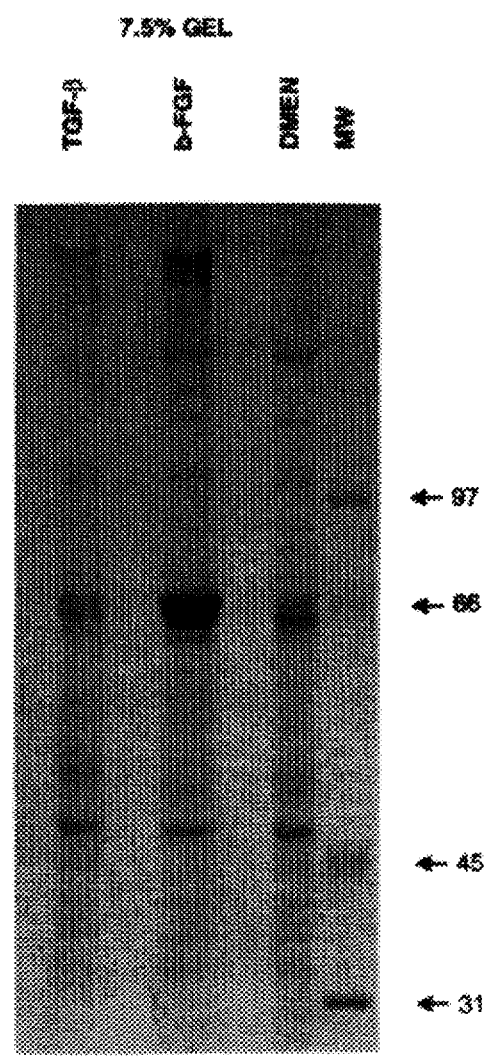
FIG. 7A 10% GEL
FIG. 7B 7.5% GEL

BRAIN ENDOTHELIAL CELL PROTEIN INDUCED BY NERVE GROWTH FACTOR

BACKGROUND OF THE INVENTION

1. Field of the Invention

The present invention relates generally to the fields of neurology and protein chemistry. More specifically, the present invention relates to a novel 67 kDa membrane protein secreted by brain endothelial cells.

2. Description of the Related Art

Nerve growth factor (NGF) plays an important role in the development and survival of sensory, sympathetic and certain cholinergic neurons. The trk protooncogene encodes a protein, gp $140^{trk}$, a membrane spanning protein tyrosine kinase, whose expression is restricted to only neural tissues. The neurotrophic receptors trk A, B & C are tyrosine kinases and are expressed in the peripheral and central nervous systems, each displaying distinctive temporal and cell specific patterns of expressions. The amount of NGF in the area of damaged or inflamed tissues is known to increase several fold and this effect is observed within hours of the initiation of the damage. NGF is involved in immunomodulation through mast cell activation and also in the tissue repair process. Brain microvascular endothelial cells along with astrocytes play an important role in maintaining the blood brain barrier (BBB). NGF's role in repairing microvascular endothelium following tissue damage requires the presence of functional NGF receptors (trk-A) on the endothelial cells to initiate angiogenesis necessary for the replacement of damaged tissues.

Two of the protooncogenes that encode nuclear proteins (c-fos, c-myc) have been implicated in growth regulatory mechanisms as they are rapidly and transiently induced following treatment of cells with polypeptide growth factors and other agents. The induction of c-fos is associated with a variety of biological events including mitogenesis, differentiation, and depolarization of neuronal cells. These observations have led to suggestions that fos plays a general role as a nuclear messenger in the signal transduction system.

The atherosclerotic lesion or atheroma has been the focus of study for many years, and the histological features have been well delineated in showing four major characteristics. These features are: (1) cellular proliferation, particularly smooth muscle cells; (2) increase in cholesterol deposition, especially cholesterol esters; (3) prominance of macrophages, particularly those which are lipid-laden, so-called "foamy cells" because of their appearance of being fat-filled, plus associated cytokines, produced by macrophages among other cellular elements including those in the blood; and (4) enhanced synthesis of connective tissue elements, such as elastin and glycosaminoglycans. Each of these four areas of histological prominence has been the focus of intense research, and while the definitive sequence of atherogenesis is still debated and uncertain, it clearly is multifactorial and includes the conspiracy of impaired cholesterol metabolism in conjunction with increased proliferation of smooth muscle cells and with heightened activity of cytokines. Certain cytokines are known to be important in regulating leukocyte adhesion, cellular growth, vasomotor functions, remodeling of the vascular matrix and regulating blood compatibility in order to minimize or influence thrombosis on arterial endothelium.

No single element provokes atherosclerosis in isolation but likely control of one of these interactive elements should assist in substantially reducing the process of atherogenesis. For example, cholesterol reduction has already made an impact in decreasing the occurrence of coronary heart disease in subjects at risk who have reduced their serum cholesterol levels below 170 mg/dl. Vascular injury, as occurs with hypertension, smoking, oral contaceptives and other insults unrelated to plasma cholesterol levels, causes the adhesion of platelets to the site of injury. This adhesion provokes a "release reaction" in platelets with the secretion of a variety of compounds, but particularly thromboxane A2 and adenosine diphosphate and mobilizes the recruitment of platelets to increase aggregation. In addition, the platelets release platelet-derived growth factor (PDGF) which provokes the proliferation of smooth muscle cells and their migration to the endothelium where the smooth muscle cells form the initial elements of an atheroma.

The atheromatous process is limited primarily to the large vessels such as the aorta and conducting arteries, such as the carotid, renal, coronary or middle cerebral arteries. However, smaller arterioles can be affected with a proliferative process as in lacunar strokes wherein fat laden cells and proliferation is termed "lipohyalinosis". Furthermore, in Binswanger's Disease or subcortical arteriopathic encephalopathy, the small penetrating arterioles of the white matter are "end vessels" in processing of unknown nature. The proliferative process of these smaller vessels may represent uncontrolled proliferation under a normally present growth factor. The normal production of nerve growth factor (NGF) by smooth muscle cells of arteries and the response of the NGF protein, the trk-oncogene, suggests a paracrine function. Aberrant or complete loss of regulation of this paracrine control could lead to increased proliferation of arteriolar smooth muscle cells and narrowed luminal area and subsequent reduced blood flow and ischemia. Thus, the normal proliferation of smooth muscle cells probably participates in atheroschlerosis and the same uncontrolled process in cerebral arterioles can lead to luminal narrowing, brain ischemia of conducting fibers and stroke-like symptoms and dementia.

The prior art is deficient in the lack of effective means of preventing or therapeutically treating a wide variety of cerebrovascular diseases. The present invention fulfills this longstanding need and desire in the art.

SUMMARY OF THE INVENTION

In one embodiment of the present invention, there is provided a composition of matter comprising an isolated and purified protein that is secreted by brain endothelial cells, having a molecular weight of approximately 67 kDa of SDS-PAGE, said protein being capable of stimulating proliferation of cerebral arteriole smooth muscle cells.

In another embodiment of the present invention, there is provided a pharmaceutical composition, comprising an isolated and purified protein that is secreted by brain endothelial cells, having a molecular weight of approximately 67 kDa of SDS-PAGE, said protein being capable of stimulating proliferation of cerebral arteriole smooth muscle cells and a pharmaceutically acceptable carrier.

In yet another embodiment of the present invention, there is provided a method of preparing the protein of the present invention, comprising the steps of: growing brain endothelial cells in a media at a temperature of about 37° C.; harvesting the cells; and isolating and purifying the protein of the present invention from said cells.

In still yet another embodiment of the present invention, there is provided a method of treating a cerebrovascular disease in a human comprising the step of administering to a human a pharmacologically effective dose of an oligonucleotide designed to inhibit the production of the protein of the present invention.

In another embodiment of the present invention, there is provided a method of improving collateral cerebrovascular circulation comprising the step of administering to a human a pharmacologically effective dose of the pharmaceutical composition of the present invention.

In yet another embodiment of the present invention, there is provided a method of determining the severity of a cerebrovascular disease in a human comprising the step of measuring the serum concentration of the protein of the present invention.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 7 shows the secretion of a 67 kDa protein in rat brain endothelial cells by bFGF.

DETAILED DESCRIPTION OF THE INVENTION

Figure 1:
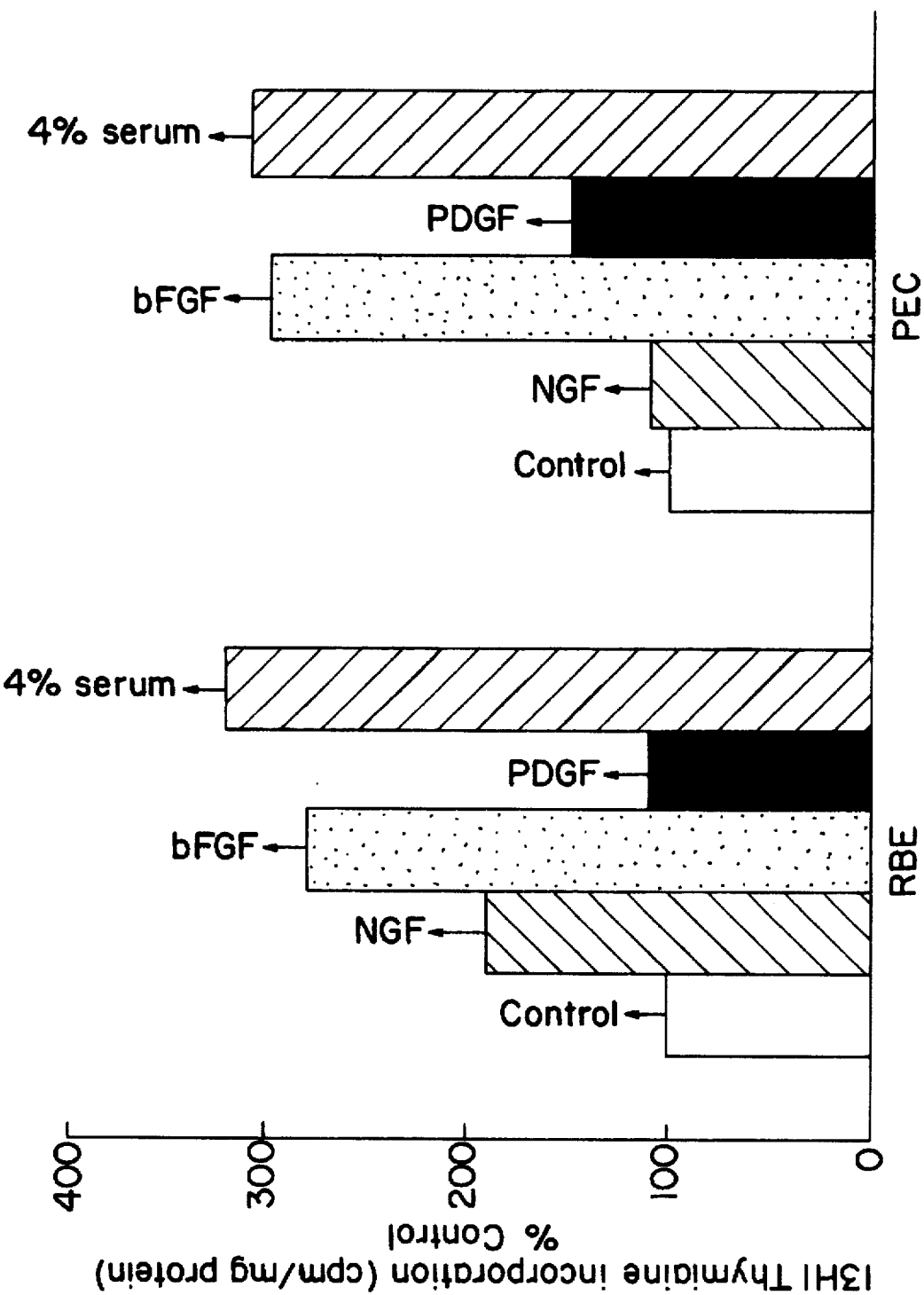
FIG. 1 shows the levels of DNA synthesis in rat brain endothelial cells (RBE) and pulmonary endothelial cells (PEC). Thymidine incorporation was measured in the presence of either nerve growth factor (NGF), basic fibroblast growth factor (bFGF), platelet derived growth factor (PDGF), 4% serum or control media.

The present invention describes immunological and PCR based quantitation of trk A expression in rat brain endothelial cells. Rat brain endothelial cells respond to nerve growth factor and the responses are seen by changes in increased thymidine incorporation, induction of genes including transcription factors (AP1) and expression of mRNA for trk A, possibly through activation of fos gene. Conditioned media of nerve growth factor-treated rat brain endothelial cells contained a protein of about 67 kDa, which provoked increased ($^{3}$H)thymidine incorporation into vascular smooth muscle cells. Among the non-neural cells, only B cells are known to be activated by NGF and result in increases in immunoglobulin production and B cell proliferation. Thus, the present invention discloses the mechanism by which NGF plays a role in brain endothelial cell angiogenesis, both in the development of collateral circulation and in smooth muscle cell proliferation.

In response to NGF exposure to brain endothelial cells, the present invention demonstrates increased synthesis of DNA and of the trkA receptor protein as well as the associated release of a unique protein having a molecular weight of 67 kDa. In addition, early gene induction (AP-1 complex) occurred. Gel shift assay using anti-fos indicated a rapid induction of the fos gene. In rat brain endothelial cells, induction of AP-1 complex after stimulation with NGF suggests that fos may function in a signal transduction system that couples short term events induced by extracellular signal to long term alterations in gene expression. The present invention discloses that NGF is a principal mediator of the release of a novel 67 kDa protein since six hour exposure of rat brain endothelial cells to nerve growth factor, grown in 25 cm$^2$ flasks, resulted in sufficient protein that could be stained with coomassie blue, whereas control cells did not. These remarkably high values of releasable protein did not change with earlier passages. Early culture, through passage 3 and 14, showed similar amounts of releasable protein although from passage 15 the pattern changed.

The unique response of rat brain endothelial cells to nerve growth factor, not seen with peripheral endothelial cells, such as pulmonary endothelial cells, has implications for both normal physiology, such as collateral circulation, and the pathological state, such as subcortical encephalopathy or Binswanger's Disease in which unregulated proliferation of smooth muscle cells in response to NGF-stimulated release of a growth factor from rat brain endothelial cells may account for end-arteriole proliferation and narrowing.

The present invention provides methods of regulating cerebral arteriole smooth muscle cell proliferation by rat brain endothelial cell. With the teachings of the present invention, one with ordinary skill in this art could manipulate genes controlling growth factors, as well as use antisense technology. Thus, the present invention would be useful in creating protective collateral circulation and minimizing arteriole narrowing and ultimately preventing strokes.

The novel protein of the present invention can, by modifying smooth muscle cell growth and proliferation, affect brain vascular stability, resilience, compliance, and integrity under normal conditions of pulsatile flow, alter the development and maintenance of collateral circulation.

These expected normal physiological functions, when aberrant or in response to external stimuli with either over- or under-expression of the protein of the present invention, may play a role in the cerebrovascular complications seen with a variety of diseases and stressors. Abnormal responses endogenously may be under responsiveness for the creation of this protein and cause brain vessels to be more fragile, as seen with certain cerebrovascular diseases such as intracerebral hemorrhage, subarachnoid hemorrhage due to aneurysms, and migraine. In addition, increased responsiveness with excess proliferation of smooth muscle cells may contribute to intracerebral atherosclerosis, lipohyalinosis, Binswanger's disease or subcortical arteriopathic encephalopathy, Moyamoya disease and impairment of the blood brain barrier with brain edema formation.

As the 67 kDa protein of the present invention is secreted by brain endothelial cells, circulating levels of this protein can be detected by radioimmunoassay. In the disease states, serum concentrations of this protein will correlate with conditions, such as Binswanger's disease, as in abnormal responsiveness to the protein. On the other hand, in normal physiological situations, such as collateral circulation formation, flow-related changes in vascular remodelling may trigger this protein's role in growth and not proliferation.

Under conditions of normal physiology and pathological conditions, control and regulation of the protein of the present invention at the cellular and molecular level can be utilized by a person having ordinary skill in this art as a means of optimizing normal vascular function and minimizing disease. Techniques currently available which may operate to modify the protein of the present invention include anti-sense oligonucleotide technology and triplex forming oligonucleotide technology. It is anticipated that drugs modifying specific promoter or enhanced regions of genes may play a similar role in the future.

It is specifically contemplated that pharmaceutical compositions may be prepared using the novel protein of the present invention. In such a case, the pharmaceutical composition comprises the novel protein of the present invention and a pharmaceutically acceptable carrier. A person having ordinary skill in this art would readily be able to determine, without undue experimentation, the appropriate dosages and routes of administration of the novel protein of the present invention.

The level of ordinary skill of the average scientist in the area of molecular biology has increased substantially in recent years. A person having ordinary skill in this art would readily be able to sequence, without undue experimentation, the novel brain endothelial protein of the present invention. With the knowledge of the protein, a person of ordinary skill could readily clone the gene encoding the protein. Knowledge of the gene sequence allows one with ordinary skill in this art to develop triplex forming oligonucleotides to inhibit transcription of the gene encoding the novel brain endothelial protein of the present invention. Knowledge of the protein sequence of brain endothelial protein of the present invention allows one to readily prepare, without undue experimentation, anti-sense oligonucleotides to inhibit translation of the protein.

Thus, the present invention provides a composition of matter comprising an isolated and purified protein that is secreted by brain endothelial cells, having a molecular weight of approximately 67 kDa of SDS-PAGE, said protein being capable of stimulating proliferation of cerebral arteriole smooth muscle cells.

A pharmaceutical composition, comprising the protein of the present invention and a pharmaceutically acceptable carrier is also provided. The pharmaceutical compositions of the present invention are suitable for use in a variety of drug delivery systems. For a brief review of present methods for drug delivery, see Langer, *Science*, 249:1527–1533 (1990). Methods for preparing administrable compounds will be known or apparent to those skilled in the art and are described in more detail, for example, in Remington's *Pharmaceutical Science*, 17th ed., Mack Publishing Company, Easton, Pa. (1988).

The present invention also provides a method of preparing the protein of claim 1, comprising the steps of: growing brain endothelial cells in a media at a temperature of about 37° C.; harvesting the cells; and isolating and purifying the protein of claim 1 from said cells. Generally, as disclosed by the present invention, the production of protein of the present invention can be stimulated by a growth factor such as nerve growth factor.

The present invention also provides a method of treating a cerebrovascular disease in a human comprising the step of administering to a human a pharmacologically effective dose of an oligonucleotide designed to inhibit the production of the protein of the present invention.

Representative examples of cerebrovascular diseases treatable by the methods of the present invention include intracerebral hemorrhage, subarachnoid hemorrhage due to aneurysms, migraine, intracerebral atherosclerosis, lipohyalinosis, Binswanger's disease or subcortical arteriopathic encephalopathy, Moyamoya disease and impairment of the blood brain barrier with brain edema formation.

A person having ordinary skill in this art would readily be able to prepare oligonucleotides, such as triplex forming oligonucleotides and anti-sense oligonucleotides, that would be useful in inhibiting or regulating the production of the protein of the present invention.

The present invention also provides a method of improving collateral cerebrovascular circulation comprising the step of administering to a human a pharmacologically effective dose of the composition of claim 2. The present invention also provides a method of determining the severity of a cerebrovascular disease in a human comprising the step of measuring the serum concentration of the protein of claim 1.

The following examples are given for the purpose of illustrating various embodiments of the present invention and are not meant to limit the present invention in any fashion.

EXAMPLE 1

Isolation of Rat Brain Endothelial Cells

Rat brain endothelial cells were isolated from newborn rat brains and cells were plated on gelatin coated dishes in culture medium containing 2% human platelet-poor plasma, 2% fetal bovine serum and 100 μg/ml endothelial cell growth factor. Colonies that exhibited endothelial morphology were subcloned and subsequently cloned and frozen cell stocks were maintained. The cells were characterized for endothelial properties including morphology, non-thrombogenic cell surface and expression of factor VIII antigen.

To illustrate the effect of NGF and other growth promoting substances on proliferative response of brain and pulmonary endothelial cells, cells were plated in 24 well tissue culture dishes and grown until 80% confluency. The cultures were growth arrested by 48 hours incubation in DMEM containing 0.1% bovine serum albumin (BSA) and 0.1% glucose. Experiments were commenced by subsequent incubation of cells in serum free DMEM in the presence or absence of growth factors. [$^3$H]-Thymidine was added and after 24 hours exposure, cell layers were washed and assayed for incorporation of tritium into DNA. FIG. 1 illustrates that the level of thymidine incorporation was enhanced by nerve growth factor in rat brain endothelial cells but not in pulmonary endothelial cells

EXAMPLE 2

TrkA Expression in Rat Brain Endothelial Cell

Figure 2:
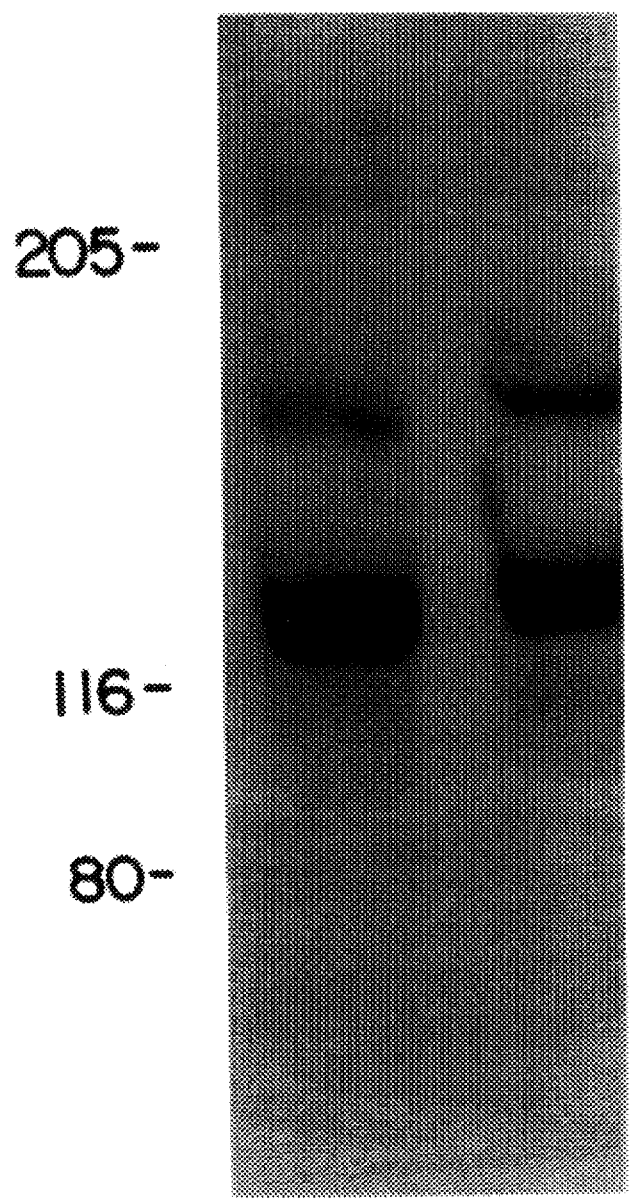
FIG. 2 shows the expression of TrkA in rat brain endothelial cells. Cell lysates were prepared from rat brain endothelial cells and PC-12 cells, polypeptides were resolved by 7.5% sodium dodecyl sulfate-polyacrylamide gel electrophoresis (SDS-PAGE) and transferred to nitrocellulose membrane. Membranes were incubated overnight with affinity purified polyclonal anti-trkA, probed for one hour with horseradish peroxidase conjugated second antibody and developed using ECL immunodetection system.

To determine the presence of NGF receptor (gp140$^{trk}$) in rat brain endothelial cells, western blot analysis using polyclonal anti-trk A, trk B and trk C were used. Rat brain endothelial cells and PC-12 cells were primed with NGF for 7 days. Cells were lysed by rocking in NP-40 lysis buffer (20 mM Tris, pH 8.0, 137 mM NaCl, 10% glycerol, 1% NP-40) containing 1 mM PMSF, 0.15 µg/ml aprotinin and 1 mM sodium orthovanadate at 4° C. for 20 minutes. Cells lysates were prepared, polypeptides were resolved by 7.5% SDS-PAGE and transferred to nitrocellulose membrane. Membranes were blocked for 1 hour and then incubated overnight with affinity purified polyclonal anti-trkA. Membranes were washed and probed for 1 hour with horseradish peroxidase conjugated second antibody and developed using ECL immunodetection system (AMERSHAM) according to the manufacturer's instructions. Immunoblot specifically positive to trk A, identified a 140 KDa protein (FIG. 2).

EXAMPLE 3

Trk Receptor Gene Expression

Figure 3:
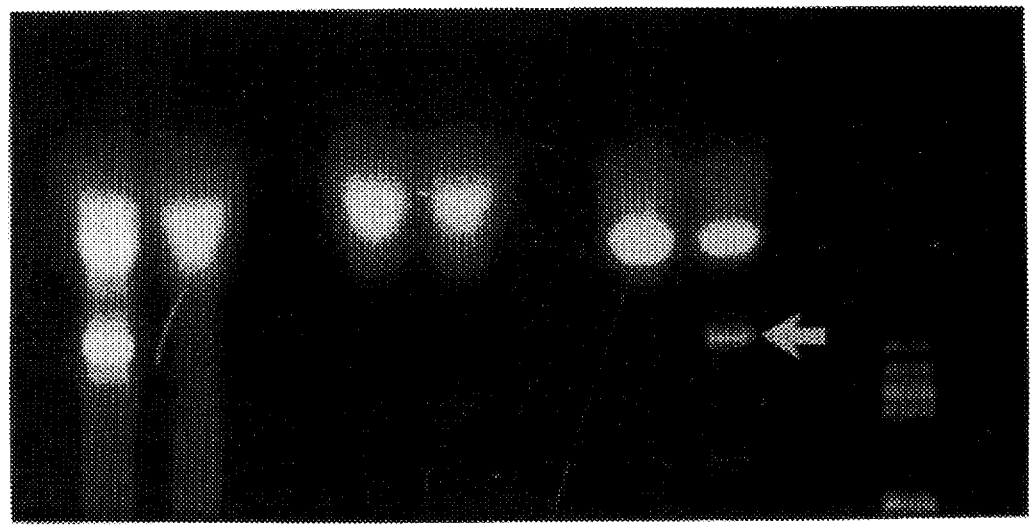
FIG. 3 shows the reverse transcriptase polymerase chain reaction (RT-PCR) product of rat brain endothelial cells and PC-12 control cells. Five µg total RNA and PC-12 cells were reverse transcribed and then amplified by PCR using trkA specific primers. Lanes: 1) PC-12 RNA; 2) PC-12 RNA+ DMSO; 3) & 4) Enzymes and template control; 5) rat brain endothelial cell RNA with DMSO; 6) rat brain endothelial cell RNA and 7) DNA marker. Two hundred (200) base pair product (indicated by the arrow) obtained with rat brain endothelial cell mRNA is identical to that of the PC-12 cells.

The expression of trk receptor gene in rat brain endothelial cells was confirmed by the presence of mRNA. Total RNA was reverse transcribed using random hexamer primers. The mixture of cDNA produced was then used as a source of template to extend a portion of trk-A gene. The primer used from cDNA encoding extracellular region of the protein was 5'-GGTCCAGGTGCCCAATGCCTCGG and 5'-AGCTGCTCTAGATCATCCTTCTTCTCCACCGG. FIG. 3 illustrates that a 200 base pair product generated by PCR was identical to the product generated by the trk-A positive PC-12 cells.

EXAMPLE 4

AP-1 Complex Activation

Figure 4:
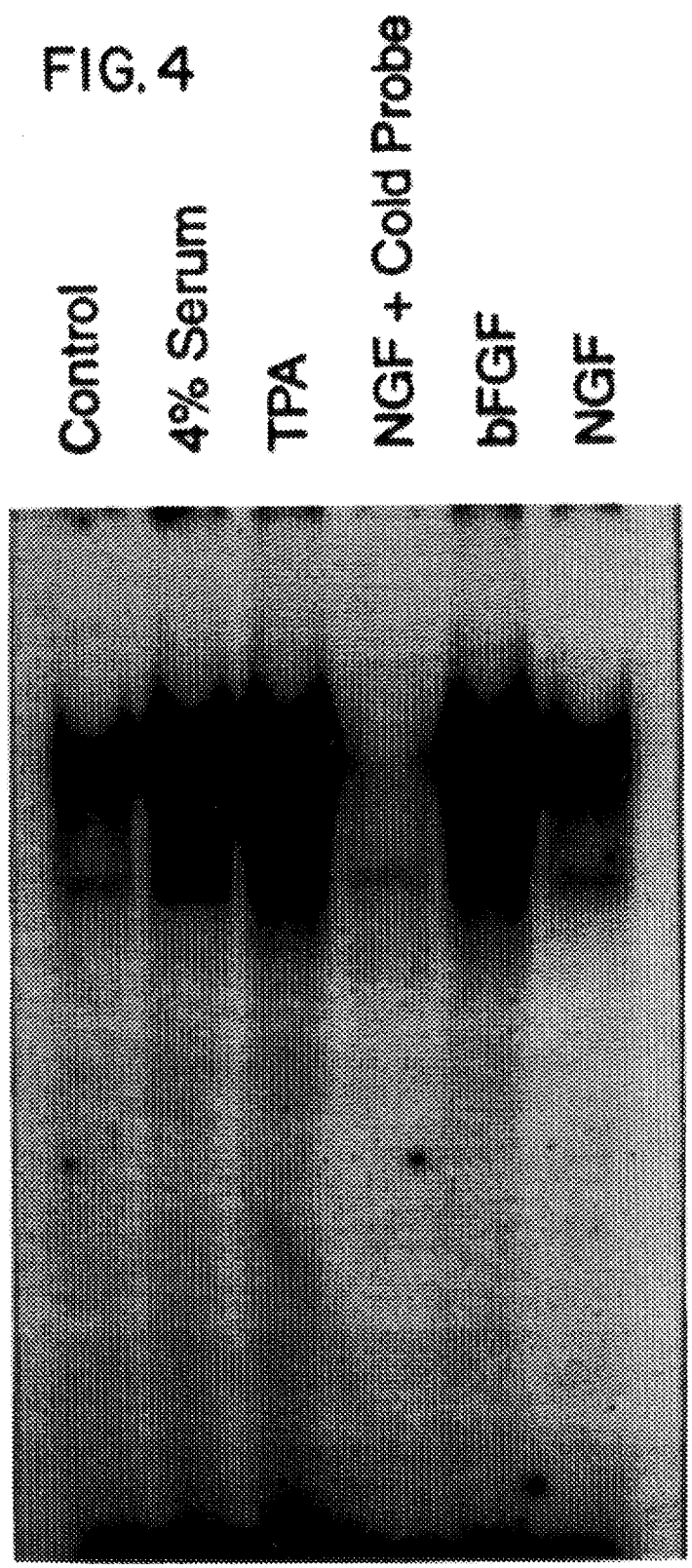
FIG. 4 shows the activation of AP-1 complex in rat brain endothelial cells by NGF. Nuclear extracts were prepared from untreated (control) or from rat brain endothelial cells treated for 15 minutes with 4% serum, 300 mM TPA, 10 ng/ml bFGF or 100 ng/ml NGF. Nuclear extracts (2 µg protein) was incubated with 2 µg poly (dI-dc) and $^{32}$P-labeled AP1 probe (0.5 ng) for 30 minutes at room temperature. The reaction mixture was loaded to 5% polyacrylamide gel and electrophoresed. The gel was dried and analyzed by autoradiography.

The effect of NGF and other growth promoting substances on AP-1 expression in rat brain endothelial cells was measured by gel mobility shift assay. (FIG. 4). Nuclear extracts were prepared from untreated (control) or from rat brain endothelial cells treated for 15 minutes with 4% serum, 300 nM TPA, 10 ng/ml bFGF or 100 ng/ml NGF. As described by Dignam et al. *Nucl. Acids Res.*, 11:1475–1489 (1983), subconfluent rat brain endothelial cells were washed with ice cold PBS and scraped into 5 ml PBS. The cells were sedimented by centrifugation (500×g for 5 minutes), then resuspended in 5 ml hypotonic solution (10 mM Tris-HCl [pH 7.9], 12.5 mM MgCl$_2$, 10 mM KCl, 0.5 mM DTT) and allowed to swell on the ice for 10 minutes. The cells were then homogenized by 20 strokes of a glass Dounce homogenizer and nuclei were sedimented by centrifugation at 1000×g for 5 minutes. The nuclei were then resuspended in the resuspension buffer (20 mM Tris-HCl [pH 7.9], 1.5 mM MgCl$_2$, 20% glycerol, 0.5 mM DTT) followed by the addition of 4M KCl to a final concentration of 0.3M KCl. The suspension was rocked gently at 4° C for 30 minutes, then centrifuged at 13000×g at 4° C. for 15 minutes. The supernatant containing the nuclear extract was stored at −70° C. until assayed.

AP-1 binding site was prepared from two oligonucleotides, consensus sequences are 5'-GATCTGTGACTCAGGGGA-3' and 5'GATCTCGCGCTGACTCACA-3'. Synthetic oligomers were end labeled according to Maniatis et al. Competitor DNAs were added at the same time the labeled fragment was added. Nuclear extracts (2–5 µg protein) were incubated with 20 µg poly (dl-dc) and the dCT-$^{32}$P-labeled API probe (0.5 ng) for 30 minutes at room temperature. The reaction mixture was loaded to 5% polyacrylamide gel (30:0.8/ acrylamide:bisacrylamide/30:0.8) gel in 0.25 TBE Trisma base, 25 mM boric acid and 1 mM EDTA) and electrophoresed. The gel was dried and analyzed by autoradiography. The density of AP-1 bands were quantitated by a Bio-Rad Imaging densitometer (Model GS-650). To determine the identity of the proteins contributing AP-1 complex, the effect of antibodies directed against c-fos and c-jun on these complexes was examined.

Figure 5:
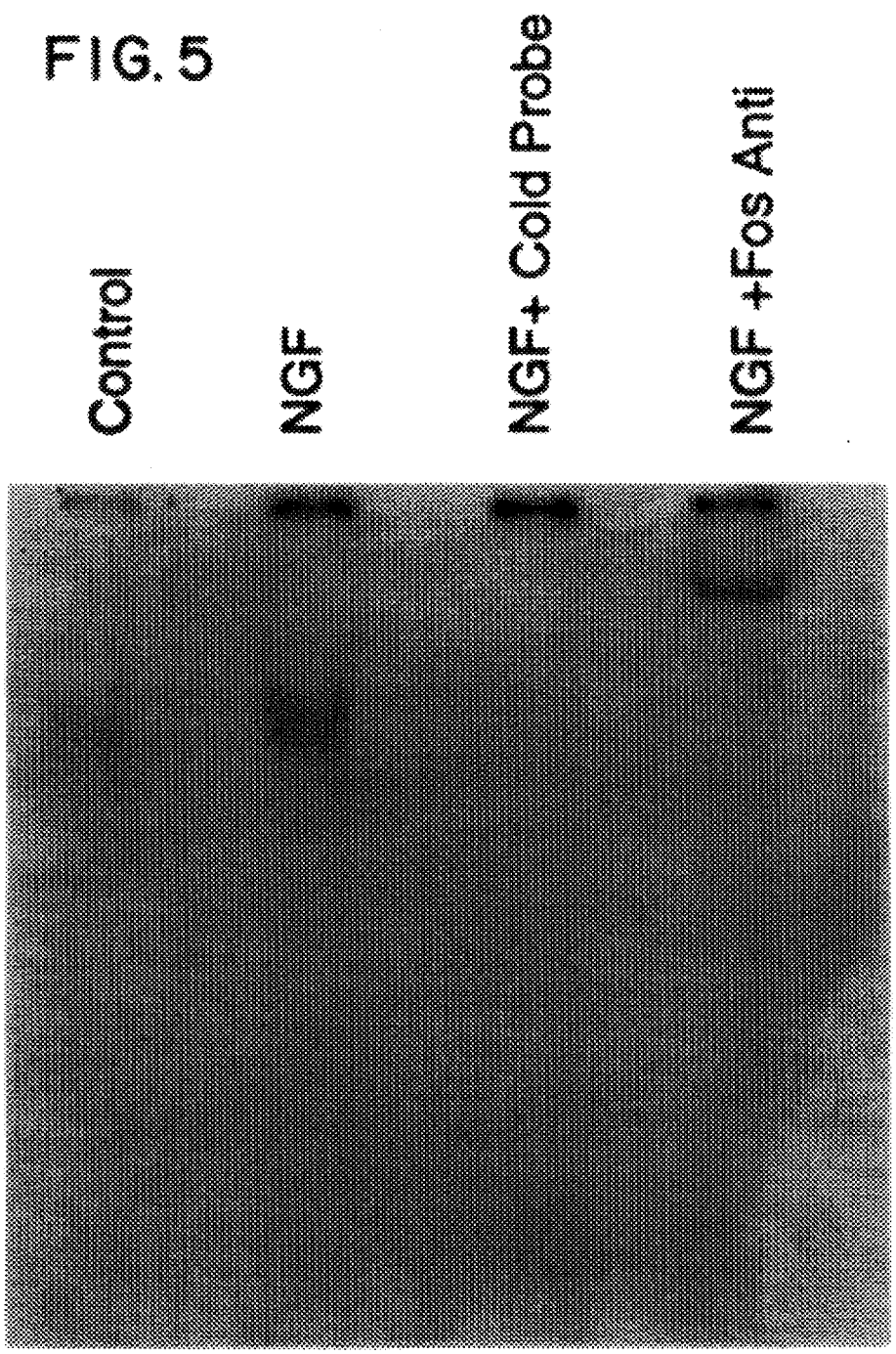
FIG. 5 shows the induction of c-fos by NGF on rat brain endothelial cells. Nuclear extracts (2 µg) from rat brain endothelial cells were preincubated with no addition (control) or with antibodies to c-fos for 16 hours. $^{32}$P-labeled AP1 (0.5 ng) was then added and the complexes were analyzed on a 5% non-denaturing gel.

It is known that specific antibodies can either disrupt or retard protein-DNA complexes in non-reducing gels. Antibodies were added to rat brain endothelial cell nuclear extracts and incubated for 16 hours at 4° C. before the addition of labeled probe. (FIG. 5) Bands indicated by arrow represent the sequence specific binding. Addition of cold probe shows specificity of binding and c-fos antibody prevents formation of normal DNA protein complex and generates in a slower migrating form.

EXAMPLE 5

NGF Stimulation of 67 kDa Protein

Figure 6:
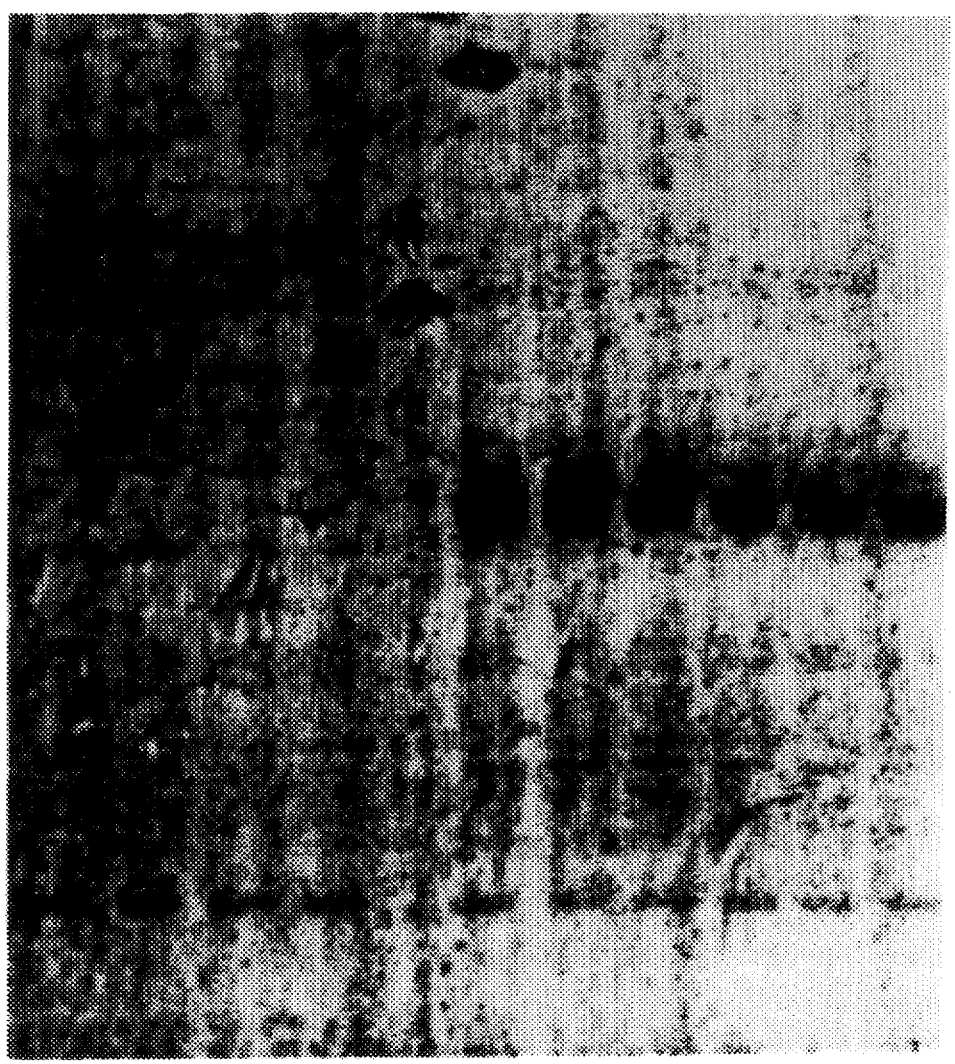
FIG. 6 shows the secretion of a 67 kDa protein in rat brain endothelial cells by NGF.

Cell surface glycoproteins are subjected to extensive modulation in vivo and some of these glycoproteins may play a pivotal role in many cellular processes. To illustrate that responses of rat brain endothelial cell to nerve growth factor is associated with such a phenomenon, conditioned media from rat brain endothelial cells were collected after exposure to nerve growth factor. Basically, cells were grown to confluence, washed extensively and exposed to NGF for 6 hours. (FIG. 6).

Media was collected and concentrated using centricon 30. Concentrated samples were subjected to 7.5% SDS-PAGE according to Laemmli and protein bands were identified by staining with coomassie blue and destained in 30% methanol/10% acetic acid (v/v). One distinct protein band (67 KDa) appeared in NGF-treated rat brain endothelial cell-conditioned media and represented approximately 80% of the total protein. Coomassie stained protein spots were then cut, subjected to V8 protease digestion, electrophoresed in a 15% acrylamide gel and electroblotted. Determination of interval amino acid sequence from the electrophoretically separated proteins was analyzed by automated sequence. The sequence of one of the peptides was:

Pro-Glu-Pro-Asp-Asp-Glu-Ala-Leu-Glu-Ala-Asn-Val-Ala-Gln.

This protein appears to have N-terminal blockage by an acyl moiety. As many as 50% of all eucaryotic proteins are blocked at the amino terminus. The sequence information of the truncated peptides did not match with the sequence of any known protein in the data bank (GEN bank).

EXAMPLE 6 bFGF Stimulation of a 67 kDa Protein

The present invention also discloses the isolation of a secretory protein from the conditioned media of rat brain endothelial cells by treating the cells with as low as 10 ng/ml of basic fibroblast growth factors (FIG. 7). This protein has almost identical electrophoretic mobility on SDS-PAGE to that of the protein obtained with nerve growth factor treatment of the rat brain endothelial cells. Basic fibroblast growth factor is known to have an angiogenic effect on rat brain endothelial cells. Thus, the bovine fibroblast growth factor-stimulated protein is likely involved in the angiogenic process of the vascular endothelium.

The basic fibroblast growth factor-stimulated protein is secreted immediately following the treatment of b-FGF and the secretion continues for at least 48 hours. It has a molecular weight of about 65–70 kDa and has the properties of a glycoprotein.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

We claim:

1. An isolated and purified protein that is secreted by rat brain endothelial cells, said protein being characterized by:

having a molecular weight of approximately 67 kDa as measured by SDS-PAGE;

being induced by nerve growth factor;

having the activity of stimulating proliferation of cerebral arteriole smooth muscle cells; and comprising the amino acid sequence:

Pro-Glu-Pro-Asp-Asp-Glu-Ala-Leu-Glu-Ala-Asn-Val-Ala-Gln (SEQ ID NO:5).

2. A composition comprising the protein of claim 1 and a carrier.

* * * * *

UNITED STATES PATENT AND TRADEMARK OFFICE
CERTIFICATE OF CORRECTION

PATENT NO. : 5,677,277
DATED : October 14, 1997
INVENTOR(S) : Frank M. Yatsu, et al It is certified that error appears in the above-identified patent and that said Letters Patent is hereby corrected as shown below:

On the title page, item [57],

In the Abstract, line 3, "of" (second occurrence) should read --on--.

In Column 1, line 15, "membrane spanning" should read --membrane-spanning--.

In Column 1, line 16, please delete the comma after the word "kinase".

In Column 1, line 47, "prominance" should read --prominence--.

In Column 2, line 5, "contaceptives" should read -- contraceptives --.

In Column 2, line 20, "fat laden" should read --fat-laden--.

In Column 2, line 35, "atheroschlerosis" should read -- atherosclerosis --.

UNITED STATES PATENT AND TRADEMARK OFFICE
CERTIFICATE OF CORRECTION

PATENT NO. : 5,677,277
DATED : October 14, 1997
INVENTOR(S) : Frank M. Yatsu, et al It is certified that error appears in the above-identified patent and that said Letters Patent is hereby corrected as shown below:

In Column 2, line 49, "of" (second occurrence) should read --on--.

In Column 2, line 56, "of" (first occurrence) should read --on--.

In Column 3, line 61, "was" should be replaced with --were--.

In Column 4, line 39, "short term" should read --short-term--.

In Column 4, line 40, "long term" should read --long-term--.

In Column 5, line 3, after the word "integrity", please insert --, and,--.

In Column 5, line 28, "remodelling" should read --remodeling--.

UNITED STATES PATENT AND TRADEMARK OFFICE
CERTIFICATE OF CORRECTION

PATENT NO. : 5,677,277
DATED : October 14, 1997
INVENTOR(S) : Frank M. Yatsu, et al It is certified that error appears in the above-identified patent and that said Letters Patent is hereby corrected as shown below:

In Column 5, line 59, "triplex forming" should read -- triplex-forming --.

In Column 6, line 2, "of" (second occurrence) should read --on--.

In Column 6, line 11, "administrable" should read --administerable--.

In Column 6, line 38, , "triplex forming" should read -- triplex-forming --.

In Column 6, line 57, "gelatin coated" should read --gelatin-coated--.

In Column 7, line 12, after the word "cells" (first occurrence), please insert a comma.

In Column 7, line 12, after the word "cells" (second occurrence), please insert a period.

UNITED STATES PATENT AND TRADEMARK OFFICE
CERTIFICATE OF CORRECTION

PATENT NO. : 5,677,277  Page 4 of 6
DATED : October 14, 1997
INVENTOR(S) : Frank M. Yatsu, et al It is certified that error appears in the above-identified patent and that said Letters Patent is hereby corrected as shown below:

In Column 7, line 12, the word "Cell" should read --Cells--. *(is)*

In Column 7, line 18, the word "analysis" should read --analyses--.

In Column 7, line 18, the word "Cells" should read --Cell--.

In Column 7, line 33, please delete the comma after the word "trk A".

In Column 7, line 42, after the word "encoding", please insert the word --the--.

In Column 7, line 43, after "TCGG", please insert -- -3'--.

In Column 7, line 44, after "CCGG" and before the period, please insert -- -3'--.

UNITED STATES PATENT AND TRADEMARK OFFICE
CERTIFICATE OF CORRECTION

PATENT NO. : 5,677,277
DATED : October 14, 1997
INVENTOR(S) : Frank M. Yatsu, et al It is certified that error appears in the above-identified patent and that said Letters Patent is hereby corrected as shown below:

In Column 8, line 11, after the "5'" and before "GATC", please insert a hyphen.

In Column 8, line 12, "end labeled" should read --end-labeled--.

In Column 8, line 30, after the word "probe", please delete the period.

In Column 8, line 30, after "(FIG. 5)", please insert a period.

In Column 8, line 33, "DNA protein" should read --DNA-protein--.

In Column 8, line 39, "in vivo" should read --*in vivo*--.

In Column 8, line 42, "is" should be replaced with --are--.

In Column 8, line 46, after the word "hours", please delete the period.

UNITED STATES PATENT AND TRADEMARK OFFICE
CERTIFICATE OF CORRECTION

PATENT NO. : 5,677,277
DATED : October 14, 1997
INVENTOR(S) : Frank M. Yatsu, et al It is certified that error appears in the above-identified patent and that said Letters Patent is hereby corrected as shown below:

In Column 8, line 54, "Coomasie stained" should read -- Coomasie-stained --.

In Column 8, line 67, "(GEN bank)" should read --(GenBank)--.

Signed and Sealed this

Twenty-seventh Day of October, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

GGTCCAGGTC CCCAATGCCT CGG        23

( 2 ) INFORMATION FOR SEQ ID NO:2:

( i ) SEQUENCE CHARACTERISTICS:
        ( A ) LENGTH: 32
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:

(F) TISSUE TYPE:
(G) CELL TYPE:
(H) CELL LINE:

(xi) SEQUENCE DESCRIPTION: SEQ ID NO:2:

AGCTGCTCTA GATCATCCTT CTTCTCCACC GG         32

(2) INFORMATION FOR SEQ ID NO:3:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(ix) FEATURE:
        (A) OTHER:

(xi) SEQUENCE DESCRIPTION: SEQ ID NO:3:

GATCTGTGAC TCAGGGGA         18

(2) INFORMATION FOR SEQ ID NO:4:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(ix) FEATURE:
        (A) OTHER:

(xi) SEQUENCE DESCRIPTION: SEQ ID NO:4:

GATCTCGCGC TGACTCACA         19

(2) INFORMATION FOR SEQ ID NO:5:

(i) SEQUENCE CHARACTERISTICS:
        (A) LENGTH: 14
        (B) TYPE: amino acid
        (C) STRANDEDNESS: single
        (D) TOPOLOGY: linear (ii) MOLECULE TYPE:

-continued

```
        ( A ) DESCRIPTION: peptide ( i i i ) HYPOTHETICAL: No ( i v ) ANTI-SENSE: No ( v ) FRAGMENT TYPE: internal fragment ( v i ) ORIGINAL SOURCE:
             ( B ) STRAIN:
             ( C ) INDIVIDUAL ISOLATE:
             ( D ) DEVELOPMENTAL STAGE:
             ( F ) TISSUE TYPE:
             ( G ) CELL TYPE:
             ( H ) CELL LINE:

( i x ) FEATURE:
             ( A ) OTHER:

( x i ) SEQUENCE DESCRIPTION: SEQ ID NO:5:

Pro  Glu  Pro  Asp  Asp  Glu  Ala  Leu  Glu  Ala  Asn  Val  Ala  Gln
 1              5                         10
```